United States Patent [19]

Giorni

[11] Patent Number: 4,632,093

[45] Date of Patent: Dec. 30, 1986

[54] SURGICAL RETRACTOR

[75] Inventor: Gastone Giorni, Sansepolcro, Italy

[73] Assignee: Brevetti Odantoiatrici S.n.c. di Miliani Maria Pia & C., Arrezo, Italy

[21] Appl. No.: 750,177

[22] Filed: Jul. 1, 1985

[30] Foreign Application Priority Data

Jul. 23, 1984 [IT] Italy .................................. 1210 A/84

[51] Int. Cl.$^4$ ............................ A61B 1/00; A61C 5/00
[52] U.S. Cl. ........................................ 128/12; 433/140
[58] Field of Search ............................ 433/140; 128/12

[56] References Cited

U.S. PATENT DOCUMENTS 641,170  1/1900  Thurmond et al. ................ 433/140
3,722,101  3/1973  Via ..................................... 433/140

Primary Examiner—Robert Peshock
Attorney, Agent, or Firm—Sandler & Greenblum

[57] ABSTRACT

The present invention provides a surgical retractor having a generally annular base. Two generally upstanding prongs extend generally upwardly at an angle from the base. The exterior surface of the base is generally concave, whereas the exterior surface of both of the prongs is generally convex. The base and prongs together form a substantially funnel-shaped structure which is adapted to be positioned over the lower dental group of a patient and to separate the cheek and tongue from a patient's teeth.

8 Claims, 2 Drawing Figures

FIG. 1.
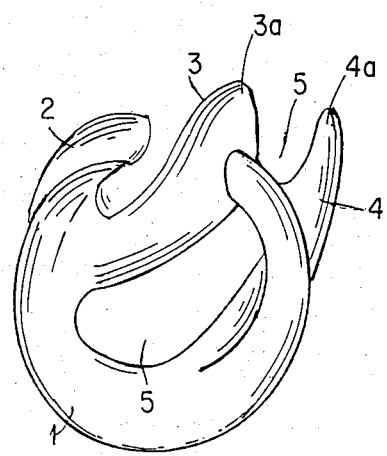
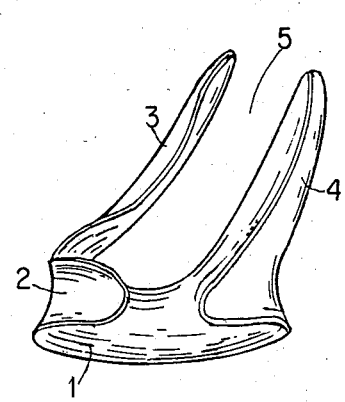
FIG. 2.

SURGICAL RETRACTOR

BACKGROUND OF THE INVENTION

1. Field of the Invention

The present invention generally relates to an odontological surgical retractor, and more specifically to a surgical retractor having a substantially conical shape. The structure is formed by an open annular base which serves to keep the dental arches of an individual spread apart. Two valves or tongues extend upwardly from the annular base and are provided to horizontally spread apart the tongue and cheek of a patient.

2. Discussion of Prior Art

The present invention relates to an odontological surgical retractor which is adapted to be fitted within the oral cavity of a patient. This retractor will permit a patient to keep his mouth in an open position and to separate or remove both the tongue and cheek of the patient from the low, lateral dental group (of teeth) over which an odontological operator must work.

Generally, odontological operators, e.g., dentists, incur difficulties in working on teeth either because: a patient is unable to keep his mouth open; or, when operating on the lower teeth groups of the patient, both the tongue and cheek of the patient are naturally inclined and thus tend to adhere to the teeth. To the contrary, the teeth which are being worked upon must be visible and free for operation in order to achieve the best results.

Several solutions to these inconveniences have been proposed. In one case, two arches were provided which were adapted to be laterally fitted to the mouth of a user between the inside labial and gingival parts, and which were inclined to keep the user's mouth open. A second system used rubber sheets which are adapted to be carved and positioned within the oral cavity of a patient to isolate teeth from the buccal portion of the patient's mouth.

In yet another system, a small lever is utilized which is adapted to be fitted into the mouth of a patient and anchored to the chin of the patient. This lever is lever is used to compress cotton rolls which are adapted to separate the cheek and tongue from the teeth of a patient.

Such well known systems did not provide a complete solution to the problems encountered by odontological operators in spacing the tongue and cheek from the tongue of a patient. These were not efficient enough and were difficult to use. They also did not perform the two desired functions of keeping the mouth at a maximum open position, and isolating the dental groups from surrounding soft tissues which must also be protected while an odontological operator is working on the teeth of a patient.

SUMMARY OF THE INVENTION

The present invention is directed to overcome the disadvantages of the prior systems. The two above-noted functions, which conventional systems do not achieve, is achieved by the present invention, which is easily and quickly applied to the mouth of a patient. It easily maintains the patient's mouth in a substantially completely open position, and does not render the patient tired during long operations performed by an odontological operator. The device also separates the cheek of a patient from the low, lateral dental groups to protect the cheek against inadvertent incisions which result from improper maneuvering with a dental drill or other odontological instruments. It also laterally removes the tongue of a patient and protects the tongue from similar damage by odontological instruments.

The present invention also is easily constructed at a reasonably low cost, and therefore can be manufactured as a a disposable item. This greatly increases the hygienic benefit of the dental device, particularly when compared to previous devices, which had to be used repeatedly after cleaning. This also results in a substantial savings in money.

The present invention is provided for in a first aspect thereof by an odontological surgical retractor comprising a substantially annular body and a first, upwardly extending prong having a first end and a second free end. The first end of said prong is attached to said annular body portion. A second prong has a first end and a second free end, said first end of said second prong being attached to said annular body. The first and second prongs are separated by an opening and the retractor is adapted to be positioned over a dental group of a patient.

The substantially annular body extends about less than 360°, and a gap is located between first and second free ends of said body.

The retractor has an inner surface defined by said body and said prongs so that the retractor will have the shape of a substantially flared funnel member.

The annular body has an exterior surface which comprises means for protecting the teeth of a patient, said outer surface being at least partially concave.

The annular body has a front portion and a rear portion and the two prongs are attached to the annular body along said rear portion.

The first prong is obliquely inclined towards the second prong, and each of the prongs can have a substantially straight profile.

The retractor is formed from a flexible and elastic material.

The present invention is provided for in a second aspect by an odontological surgical retractor comprising a generally annular base portion. The generally annular base portion has an outer convex surface, an inner substantially concave surface, and first and second generally upstanding prongs. The first prong has a first end and a second free end, a generally convex exterior surface and a substantially concave interior surface which extends upwardly from said base. The first end of said first prong is attached to said base, and is angled generally obliquely from said base towards said second prong. The first and second flanges are separated by an elongated slot, said second flange having a first end and a second free end, said first end of said second flange being attached to said base, said elongated slot extending from said base to said second ends of said prongs.

BRIEF DESCRIPTION OF THE DRAWINGS

The present invention is discussed in greater detail hereinafter with respect to the drawings, in which like reference numerals are used to describe similar parts throughout, and which illustrate a retractor which is adapted to be positioned within the low lateral dental groups of a patient; the drawings are not intended to limitate the scope of the present invention, and in the drawings:

FIG. 1 is a perspective view of an ontological surgical retractor formed in accordance with the present invention; and FIG. 2 is a top perspective view of the ontological retractor of the present invention.

DETAILED DESCRIPTION OF THE DRAWINGS

The Figs. illustrate a dental retractor; the dental retractor illustrated in FIGS. 1 and 2 is provided to be positioned within the lower left dental groups of the patient. If it is rotated about 180°, or realigned so that its valves or tongues are inverted with respect to the annular body of the retractor, it will then be possible to position a retractor formed in such fashion within the lower right lateral dental groups of a patient.

The retractor of the present invention essentially comprises a generally annular body 1; the retractor is substantially outwardly flared, in the shape of a funnel. The funnel has an exterior surface which is slightly concave in its cross-sectional configuration. With this shape, the retractor comprises a seat to be positioned on teeth of a patient; the concave cross-sectional area makes the retractor particularly stable when positioned between the dental arches of a patient, even under the retractable action of the oral muscles of the mouth of a patient. Annular body 1 extends about approximately 360°; a small gap is located between free first and second ends of the annular body.

A pair of shaped valves, prongs or tongues 3 and 4 are also provided, as illustrated in FIGS. 1 and 2. These prongs are integral with, and extend upwardly from, annular body 1. Prong 3 is provided to act on the tongue of a user by moving the tongue laterally. The second prong 4 is provided to adhere to the cheek of a user and to move the cheek away from the dental group of a patient as well as to protect the cheek against accidental shocks caused by the instruments used by an ontological operator during operations within the oral cavity.

Prongs 3 and 4 extend generally upwardly from the substantially annular base portion 1 of the device. These prongs extend upwardly from the body or base portion 1, in a generally parallel fashion; however, prong 3 is preferably obliquely inclined towards prong 4 along the rear portion of annular body 1. Both have substantially convex surfaces, as viewed from the exterior of the device. They are spaced at their respective free ends by cavity or slot 5, which extends from annular base 1 to free ends 3a and 4a; and the prongs are therefore adapted to space appropriate groups of teeth. The exterior surfaces of the teeth are protected by the valves themselves. The retractor of the present invention is advantageously formed from a flexible material so that it is adapted to conform in shape to the anatomical configuration of the oral cavity of a particular patient. It is capable of being slightly deformed and fitted, by the strength of the ontological operator, between the dental arches of a patient in such a way that the natural pressure exerted by the mouth, caused by the musculature of the mouth of a patient, will establish and fix the retractor within the oral cavity of a user.

Similarly, the valves, prongs or tongues of the retractor can be bent or deformed and will therefore assume a natural position which will substantially conform to the shape of the interior oral cavity of a patient. This will minimize the need for providing retractors of different shapes and sizes.

Preferably two models of the retractor will be provided, i.e., a right-handed model and a left-handed model. If only one model were produced, it could be used on both sides of a patient's mouth by being rotated about 180°; use of a single retractor in this fashion would structurally reduce the space within the oral cavity within which an odontological operator must perform, and would be less able to conform to the shape of a user's mouth.

Although the present invention has been described with respect to a single embodiment, it is clear that one of ordinary skill in the art would recognize that there are many equivalents to this invention and that these equivalents and embodiments are within the scope of the present invention.

What is claimed is:

1. An odontological surgical retractor comprising a substantially annular body, a first, upwardly extending prong having a first end and a second free end, said first end of the first prong being attached to said annular body, a second prong having a first end and a second end, said first end of said second prong being attached to said annular body, said first and second prongs being separated by an opening, said retractor being adapted to be positioned over a dental group of teeth of a patient, said substantially annular body extending about less than 360° and having first and second free ends separated by a gap, said retractor having an interior surface defined by said annular body and said first and second prongs, said inner surface comprising a substantially flared funnel member.

2. A surgical retractor in accordance with claim 1 wherein said annular body has a concave exterior surface, said exterior surface comprising means for protecting the teeth of a patient and for maintaining the retractor in a stable position within the mouth of a patient.

3. A surgical retractor in accordance with claim 1 wherein said annular body has a front portion and a rear portion and wherein said two prongs are attached to said annular body along said rear portion.

4. A surgical retractor in accordance with claim 1 wherein said first prong is obliquely inclined towards said second prong.

5. A surgical retractor in accordance with claim 1 wherein each of said prongs has a substantially straight profile.

6. A surgical retractor in accordance with claim 1 wherein said retractor is formed from a flexible and elastic material, said retractor being capable of conforming in shape to the anatomical configuration of the mouth of a patient.

7. An odontological surgical retractor comprising a generally annular base portion, said generally annular base portion having an outer convex surface and an inner substantially concave surface, and first and second generally upstanding prongs, said first prong having a first end and a second free end, said first prong having a generally convex exterior surface and a substantially concave interior surface and extending upwardly from said base, said first end of said first prong being attached to said base, said first prong being angled generally obliquely from said base towards said second prong, said first and second prongs being separated by an elongated slot, said second flange having a first end and a second free end, said first end of said second flange being attached to said base, said elongated slot extending from said base to said second ends of said prongs.

8. An odontological surgical retractor comprising a substantially annular body, a first, upwardly extending prong having a first end and a second free end, said first end of said first prong being attached to said annular body, a second prong having a first end and a second end, said first end of said second prong being attached to said annular body, said first and second prongs being separated by an opening, said retractor being adapted to be positioned over a dental group of teeth of a patient, each of said prongs and said annular body having a substantially concave exterior surface, said retractor comprising a substantially outwardly flared funnel member.

* * * * *